(12) United States Patent
DeCarlo

(10) Patent No.: US 8,246,614 B2
(45) Date of Patent: Aug. 21, 2012

(54) HIGH-STRENGTH MICROWAVE ANTENNA COUPLING

(75) Inventor: Arnold V. DeCarlo, Frederick, CO (US)

(73) Assignee: Vivant Medical, Inc., Boulder, CO (US)

( * ) Notice: Subject to any disclaimer, the term of this patent is extended or adjusted under 35 U.S.C. 154(b) by 686 days.

(21) Appl. No.: 12/399,222

(22) Filed: Mar. 6, 2009

(65) Prior Publication Data
US 2009/0264877 A1    Oct. 22, 2009

Related U.S. Application Data

(60) Provisional application No. 61/045,678, filed on Apr. 17, 2008.

(51) Int. Cl.
*A61B 18/18* (2006.01)
*F16B 39/02* (2006.01)

(52) U.S. Cl. .......................................... 606/33; 411/325

(58) Field of Classification Search .............. 606/27–50; 607/101–102, 156; 604/19–22; 128/898; 403/6–8, 43–48, 220–229, 292, 297, 298, 403/344; 439/314, 784; 285/248, 341, 370, 285/397, 34, 35, 392; 339/90; 411/354, 411/383, 418, 419, 900, 901
See application file for complete search history.

(56) References Cited

U.S. PATENT DOCUMENTS

| | | | |
|---|---|---|---|
| 3,551,880 A * | 12/1970 | Hartwell | ................ 439/314 |
| 3,631,363 A | 12/1971 | Miller | |
| 4,397,313 A | 8/1983 | Vaguine | |
| 4,462,412 A | 7/1984 | Turner | |
| 4,572,190 A | 2/1986 | Azam et al. | |
| 4,798,215 A | 1/1989 | Turner | |
| 5,090,857 A * | 2/1992 | Dunn | ................ 411/385 |
| 5,097,844 A | 3/1992 | Turner | |
| 5,129,396 A | 7/1992 | Rosen et al. | |
| 5,405,346 A | 4/1995 | Grundy et al. | |
| 5,417,210 A | 5/1995 | Funda et al. | |
| 5,634,754 A * | 6/1997 | Weddendorf | ................ 411/354 |
| 5,800,494 A | 9/1998 | Campbell et al. | |
| 5,957,969 A | 9/1999 | Warner et al. | |

(Continued)

FOREIGN PATENT DOCUMENTS

DE     390937     3/1924

(Continued)

OTHER PUBLICATIONS

U.S. Appl No. 10/244,346, filed Sep. 16, 2002.

(Continued)

*Primary Examiner* — Michael Peffley
*Assistant Examiner* — Khadijeh Vahdat

(57) ABSTRACT

Microwave antenna assemblies incorporating a high-strength antenna coupler are described herein. The microwave antenna has a radiating portion connected by a feedline to a power generating source, e.g., a generator. Proximal and distal radiating portions of the antenna assembly are separated by a microwave antenna coupler. In embodiments, the described antenna coupler includes a dielectric member and at least one discrete coupling member. The coupling member isolates coupling forces, such as tension and torque, from the dielectric member, which may prevent cracking and reduce the incidence of mechanical failure of the dielectric. The coupling member may be formed from high strength materials, such as stainless steel, allowing greater coupling forces to be achieved when compared to couplers using only dielectric materials. The coupling member may additionally include reinforcing members which extend into the dielectric member for increased strength.

22 Claims, 10 Drawing Sheets

U.S. PATENT DOCUMENTS

| | | | |
|---|---|---|---|
| 5,961,871 A | 10/1999 | Bible et al. | |
| 6,031,375 A | 2/2000 | Atalar et al. | |
| 6,047,216 A | 4/2000 | Carl et al. | |
| 6,086,544 A | 7/2000 | Hibner et al. | |
| 6,223,086 B1 | 4/2001 | Carl et al. | |
| 6,226,553 B1 | 5/2001 | Carl et al. | |
| 6,273,862 B1 | 8/2001 | Privitera et al. | |
| 6,375,606 B1 | 4/2002 | Garibaldi et al. | |
| 6,485,486 B1 | 11/2002 | Trembly et al. | |
| 6,496,736 B1 | 12/2002 | Carl et al. | |
| 6,547,788 B1 | 4/2003 | Maguire et al. | |
| 6,603,994 B2 | 8/2003 | Wallace et al. | |
| 6,725,080 B2 | 4/2004 | Melkent et al. | |
| 6,878,147 B2 | 4/2005 | Prakash et al. | |
| 6,956,164 B2 | 10/2005 | Brown | |
| 6,997,925 B2 | 2/2006 | Maguire et al. | |
| 7,128,739 B2 | 10/2006 | Prakash et al. | |
| 7,147,632 B2 | 12/2006 | Prakash et al. | |
| 7,234,977 B2 | 6/2007 | Westlund et al. | |
| 7,311,703 B2 | 12/2007 | Turovskiy et al. | |
| 7,318,824 B2 | 1/2008 | Prakash et al. | |
| 7,439,736 B2 | 10/2008 | Meaney et al. | |
| 7,467,015 B2 | 12/2008 | Van der Weide | |
| 7,565,207 B2 | 7/2009 | Turner et al. | |
| 2001/0047183 A1 | 11/2001 | Privitera et al. | |
| 2002/0022836 A1 | 2/2002 | Goble et al. | |
| 2003/0078614 A1* | 4/2003 | Salahieh et al. | 606/200 |
| 2004/0097805 A1 | 5/2004 | Verard et al. | |
| 2004/0242992 A1 | 12/2004 | Hareyama | |
| 2004/0267297 A1 | 12/2004 | Malackowski | |
| 2005/0149010 A1 | 7/2005 | Turovskiy et al. | |
| 2006/0264923 A1 | 11/2006 | Prakash et al. | |
| 2006/0282069 A1 | 12/2006 | Prakash et al. | |
| 2006/0293650 A1* | 12/2006 | Prakash et al. | 606/33 |
| 2007/0233057 A1 | 10/2007 | Konishi | |
| 2007/0288079 A1 | 12/2007 | Van der Weide et al. | |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 481 685 | 4/1992 |
| EP | 0 521 264 | 1/1993 |
| EP | 0 541 930 | 5/1993 |
| EP | 0 556 705 | 8/1993 |
| EP | 0 558 429 | 9/1993 |
| EP | 0 572 131 | 12/1993 |
| EP | 0 836 868 | 4/1998 |
| EP | 1 159 926 | 5/2001 |
| EP | 1 278 007 | 1/2003 |
| EP | 1 810 627 | 7/2007 |
| FR | 179607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | WO97/41924 | 11/1997 |
| WO | WO97/43971 | 11/1997 |
| WO | WO00/48672 | 8/2000 |
| WO | WO00/51513 | 9/2000 |
| WO | WO01/01847 | 1/2001 |
| WO | WO01/74252 | 10/2001 |
| WO | WO02/45790 | 6/2002 |
| WO | WO02/061880 | 8/2002 |
| WO | 03/039385 A2 | 5/2003 |
| WO | WO2004/112628 | 12/2004 |
| WO | 2005/011049 | 2/2005 |
| WO | WO2005/016119 | 2/2005 |

OTHER PUBLICATIONS

U.S. Appl No. 11/053,987, filed Feb. 8, 2005.
U.S. Appl No. 12/023,606, filed Jan. 31, 2008.
U.S. Appl No. 12/129,482, filed May 29, 2008.
U.S. Appl No. 12/135,425, filed Jun. 9, 2008.
U.S. Appl No. 12/135,690, filed Jun. 9, 2008.
U.S. Appl No. 12/147,093, filed Jun. 26, 2008.
U.S. Appl No. 12/181,504, filed Jul. 29, 2008.
U.S. Appl No. 12/184,556, filed Aug. 1, 2008.
U.S. Appl No. 12/194,254, filed Aug. 19, 2008.
U.S. Appl No. 12/197,601, filed Aug. 25, 2008.
U.S. Appl No. 12/197,405, filed Aug. 25, 2008.
U.S. Appl No. 12/197,473, filed Aug. 25, 2008.
U.S. Appl No. 12/199,935, filed Aug. 28, 2008.
U.S. Appl No. 12/203,474, filed Sep. 3, 2008.
U.S. Appl No. 12/236,686, filed Sep. 24, 2008.
U.S. Appl No. 12/244,850, filed Oct. 3, 2008.
U.S. Appl No. 12/250,110, filed Oct. 13, 2008.
U.S. Appl No. 12/250,171, filed Oct. 13, 2008.
U.S. Appl No. 12/253,457, filed Oct. 17, 2008.
U.S. Appl No. 12/277,951, filed Nov. 25, 2008.
U.S. Appl No. 12/350,292, filed Jan. 8, 2009.
U.S. Appl No. 12/351,633, filed Jan. 9, 2009.
U.S. Appl No. 12/353,623, filed Jan. 14, 2009.

U.S. Appl No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.

Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Cosman et al., "Methods of Making Nervous System Lesions" in William RH, Rengachary SS (eds): Neurosurgery, New York: McGraw•Hill, vol. 111, (1984), pp. 2490-2499.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline Product Literature, "Light Key: Visualize a Virtual Keyboard. One With No Moving Parts", 4 pages.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Heniford et al., "Initial Results with an Electrothermal Bipolar Vessel Sealer" Surgical Endoscopy (2001) 15:799-801.
Herman et al., "Laparoscopic Intestinal Resection With the LigaSure™ Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.
Jarrett et al., "Use of the LigaSure™ Vessel Sealing System for Peri-Hilar Vessels in Laparoscopic Nephrectomy" Sales/Product Literature 2000.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General, Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, pp. 205-210.

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Int'l Federation of Gynecology and Obstetrics FIGO World Congress 2000, Washington, DC.

MDTECH product literature (Mar. 2000) I'D Wire: product description, 1 page.

MDTECH product literature (Dec. 1999) "FlexStrand": product description, 1 page.

Medtrex Brochure "The O.R. Pro 300" 1 page, Sep. 1998.

Michael Choti, "Abdominoperineal Resection with the LigaSure™ Vessel Sealing System and LigaSure™ Atlas 20 cm Open Instrument" Innovations That Work, Jun. 2003.

Muller et al., "Extended Left Hemicolectomy Using the LigaSure™ Vessel Sealing System" Innovations That Work. LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.

Organ, L W., "Electrophysiologic Principles of Radiofrequency Lesion Making" Appl. Neurophysiol, vol. 39: pp. 69-76 (1976/77).

P.R. Stauffer et al., "Interstitial Heating Technologies", Thermoradiotheray and Thermochemotherapy (1995) vol. I, Biology, Physiology, Physics, pp. 279-320.

Palazzo et al., "Randomized clinical trial of LigaSure™ versus open haemorrhoidectomy" British Journal of Surgery 2002,89,154-157

"Innovations in Electrosurgery" Sales/Product Literature; Dec. 31, 2000.

Paul G. Horgan, "A Novel Technique for Parenchymal Division During Hepatectomy" The American Journal of Surgery, vol. 181, No. 3, Oapril 2001, pp. 236-237.

Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

Valleylab Brochure, "Reducing Needlestick Injuries in the Operating Room" 1 page, Mar. 2001.

Reidenbach, (1995) "First Experimental Results with Special Applicators for High-Frequency Interstitial Thermotherapy", Society Minimally Invasive Therapy, 4(Suppl I):40 (Abstr).

Richard Wolf Medical Instruments Corp. Brochure, "Kleppinger Bipolar Forceps & Bipolar Generator" 3 pages, Jan. 1989.

Rothenberg et al., "Use of the LigaSure™ Vessel Sealing System in Minimally Invasive Surgery in Children" Int'l Pediatric Endosurgery Group (I PEG) 2000.

Sayfan et al., "Sutureless Closed Hemorrhoidectomy: A New Technique" Annals of Surgery, vol. 234, No. 1, Jul. 2001, pp. 21-24.

Sengupta et al., "Use of a Computer-Controlled Bipolar Diathermy System in Radical Prostatectomies and Other Open Urological Surgery" ANZ Journal of Surgery (2001)71.9 pp. 538-540.

Sigel et al., "The Mechanism of Blood Vessel Closure by High Frequency Electrocoagulation" Surgery Gynecology & Obstetrics, Oct. 1965 pp. 823-831.

Solbiati et al., (2001) "Percutaneous Radio-frequency Ablation of Hepatic Metastases from Colorectal Cancer: Long-term Results in 117 Patients", Radiology, vol. 221, pp. 159-166.

Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.

Stuart W. Young, Nuclear Magnetic Resonance Imaging—Basic Principles, Raven Press, New York, 1984.

Sugita et al., "Bipolar Coagulator with Automatic Thermocontrol" J. Neurosurg., vol. 41, Dec. 1944, pp. 777-779.

Sylvain Labonte et al., "Monopole Antennas for Microwave Catheter Ablation", IEEE Trans. on Microwave Theory and Techniques, vol. 44, No. 10, pp. 1832-1840, Oct. 1995.

T. Matsukawa et al., "Percutaneous Microwave Coagulation Therapy in Liver Tumors", Acta Radiologica, vol. 38, pp. 410-415, 1997.

T. Seki et al., (1994) "Ultrasonically Guided Percutaneous Microwave Coagulation Therapy for Small Hepatocellular Carcinoma," Cancer 74(3):817-825.

S. Humphries Jr. et al., "Finite-Element Codes to Model Electrical Heating and Non-Llnear Thermal Transport in Biological Media", Proc. ASME HTD-355, 131 (1997).

Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.

Urrutia et al., (1988). "Retractable-Barb Needle for Breast Lesion Localization: Use in 60 Cases," Radiology 169(3):845-847.

Valleylab Brochure, "Valleylab Electroshield Monitoring System" 2 pages, Nov. 1995.

ValleyLab Brochure, "Electosurgery: A Historical Overview", Innovations in Electrosurgery, 1999.

Vallfors et al., "Automatically Controlled Bipolar Electrocoagulation—'COA-COMP'" Neurosurgical Review 7:2-3 (1984) pp. 187-190.

W. Scott Helton, "LigaSure™ Vessel Sealing System: Revolutionary Hemostasis Product for General Surgery" Sales/Product Literature 1999.

Wald et al., "Accidental Burns", JAMA, Aug. 16, 1971, vol. 217, No. 7, pp. 916-921.

Walt Boyles, "Instrumentation Reference Book", 2002, Butterworth-Heinemann, pp. 262-264.

European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.

European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
Esterline Product Literature, "Light Key: Visualize a Virtual Keyboard. One With No Moving Parts", Nov. 1, 2003; 4 pages.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.

* cited by examiner

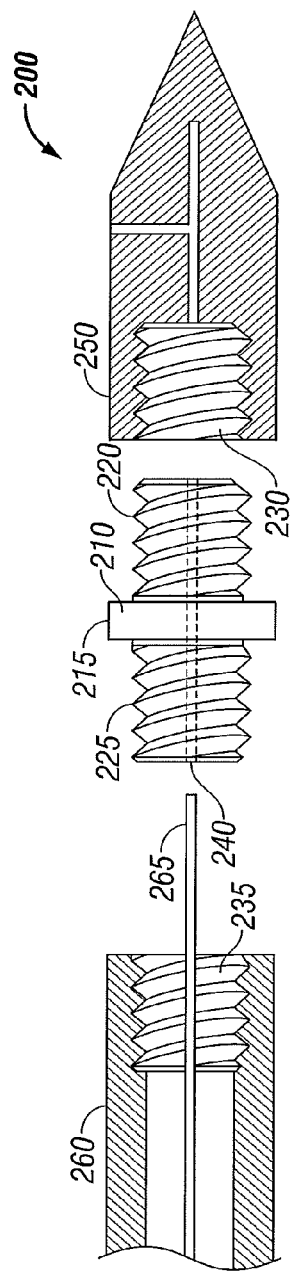
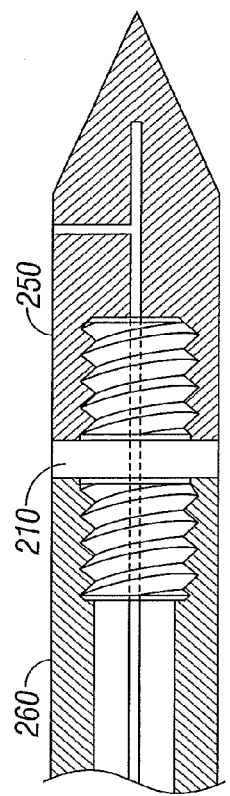
FIG. 2A
FIG. 2B

Section A-A

Section B-B

Section C-C

Section D-D

HIGH-STRENGTH MICROWAVE ANTENNA COUPLING

CROSS-REFERENCE TO RELATED APPLICATIONS

This application claims the benefit of priority to U.S. Provisional Application Ser. No. 61/045,678 entitled "HIGH-STRENGTH MICROWAVE ANTENNA COUPLING" filed Apr. 17, 2008 by Arnold V. DeCarlo, which is incorporated by reference herein.

BACKGROUND

1. Technical Field

The present disclosure relates generally to microwave surgical devices having a microwave antenna which may be inserted directly into tissue for diagnosis and treatment of diseases. More particularly, the present disclosure is directed to an insulated coupler for coupling the distal and proximal elements of a microwave antenna.

2. Background of Related Art

In the treatment of diseases such as cancer, certain types of cancer cells have been found to denature at elevated temperatures (which are slightly lower than temperatures normally injurious to healthy cells). These types of treatments, known generally as hyperthermia therapy, typically utilize electromagnetic radiation to heat diseased cells to temperatures above 41° C. while maintaining adjacent healthy cells at lower temperatures where irreversible cell destruction will not occur. Other procedures utilizing electromagnetic radiation to heat tissue also include ablation and coagulation of the tissue. Such microwave ablation procedures, e.g., such as those performed for menorrhagia, are typically done to ablate and coagulate the targeted tissue to denature or kill the tissue. Many procedures and types of devices utilizing electromagnetic radiation therapy are known in the art. Such microwave therapy is typically used in the treatment of tissue and organs such as the prostate, heart, and liver.

One non-invasive procedure generally involves the treatment of tissue (e.g., a tumor) underlying the skin via the use of microwave energy. The microwave energy is able to non-invasively penetrate the skin to reach the underlying tissue. However, this non-invasive procedure may result in the unwanted heating of healthy tissue. Thus, the non-invasive use of microwave energy requires a great deal of control.

Presently, there are several types of microwave probes in use, e.g., monopole, dipole, and helical. One type is a monopole antenna probe, which consists of a single, elongated microwave conductor exposed at the end of the probe. The probe is typically surrounded by a dielectric sleeve. The second type of microwave probe commonly used is a dipole antenna, which consists of a coaxial construction having an inner conductor and an outer conductor with a dielectric junction separating a portion of the inner conductor, which may be coupled to a portion corresponding to a first dipole radiating portion, and a portion of the outer conductor which may be coupled to a second dipole radiating portion. The dipole radiating portions may be configured such that one radiating portion is located proximally of the dielectric junction, and the other portion is located distally of the dielectric junction. In the monopole and dipole antenna probe, microwave energy generally radiates perpendicularly from the axis of the conductor.

The typical microwave antenna has a long, thin inner conductor which extends along the axis of the probe and is surrounded by a dielectric material and is further surrounded by an outer conductor around the dielectric material such that the outer conductor also extends along the axis of the probe. In another variation of the probe, which provides for effective outward radiation of energy or heating, a portion or portions of the outer conductor can be selectively removed. This type of construction is typically referred to as a "leaky waveguide" or "leaky coaxial" antenna. Another variation on the microwave probe involves having the tip formed in a uniform spiral pattern, such as a helix, to provide the necessary configuration for effective radiation. This variation can be used to direct energy in a particular direction, e.g., perpendicular to the axis, in a forward direction (i.e., towards the distal end of the antenna), or a combination thereof.

Invasive procedures and devices have been developed in which a microwave antenna probe may be either inserted directly into a point of treatment via a normal body orifice or percutaneously inserted. Such invasive procedures and devices potentially provide better temperature control of the tissue being treated. Because of the small difference between the temperature required for denaturing malignant cells and the temperature injurious to healthy cells, a known heating pattern and predictable temperature control is important so that heating is confined to the tissue to be treated. For instance, hyperthermia treatment at the threshold temperature of about 41.5° C. generally has little effect on most malignant growth of cells. However, at slightly elevated temperatures above the approximate range of 43° C. to 45° C., thermal damage to most types of normal cells is routinely observed. Accordingly, great care must be taken not to exceed these temperatures in healthy tissue.

However, many types of malignancies are difficult to reach and treat using non-invasive techniques or by using invasive antenna probes designed to be inserted into a normal body orifice, i.e., an easily accessible body opening. These types of conventional probes may be more flexible and may also avoid the need to separately sterilize the probe; however, they are structurally weak and typically require the use of an introducer or catheter to gain access to within the body. Moreover, the addition of introducers and catheters necessarily increase the diameter of the incision or access opening into the body thereby making the use of such probes more invasive and further increasing the probability of any complications that may arise.

Structurally stronger invasive probes exist and are typically long, narrow, needle-like antenna probes which may be inserted directly into the body tissue to directly access a site of a tumor or other malignancy. Such rigid probes generally have small diameters that aid not only in ease of use but also reduce the resulting trauma to the patient. A convenience of rigid antenna probes capable of direct insertion into tissue is that the probes may also allow for alternate additional uses given different situations. However, such rigid, needle-like probes may experience difficulties in failing to provide uniform patterns of radiated energy; and may fail to provide uniform heating axially along and radially around an effective length of the probe. Accordingly, it may be difficult to otherwise control and direct the heating pattern when using such probes.

Additionally, a dielectric junction used to separate portions of a rigid probe may be subjected to bending, compression, and rotational forces during manufacture, and during use. These forces may lead to failure of the junction, particularly where the dielectric junction includes an integrally formed coupling member, such as a threaded or ribbed section. Such threads or ribs often have edges which may cause stress concentrations induced by manufacturing or operational forces, causing mechanical or electrical failure of the dielectric junction. This effect is exacerbated by the structural properties of suitable dielectric materials, such as porcelain or other ceramic materials, which tend to be brittle.

SUMMARY

The present disclosure provides a high-strength microwave antenna coupler assembly and methods of use therefor, e.g., in microwave antenna assemblies used in tissue ablation applications. In some variations, the microwave antenna assembly has proximal and distal radiating portions. The coupler assembly may be a junction member that couples the proximal and distal radiation sections. At least a portion of the coupler assembly may be disposed between the proximal and distal radiating portions. The distal end of the distal radiating portion may have a tapered end which terminates at a tip configured to allow for the direct insertion into tissue with minimal resistance. An inner and an outer conductor extend through the proximal radiating portion, with the inner conductor disposed within the outer conductor. The inner conductor may extend through a channel disposed longitudinally in the coupler assembly. The inner conductor may further extend at least partially into the distal radiating portion The microwave antenna assembly may also be connected to a source of microwave energy.

The coupler includes a dielectric member and at least one discrete coupling member that is joined with the dielectric member. In embodiments, the dielectric member and the coupling member are formed from dissimilar materials. Additionally or alternatively, the dielectric member and the coupling member may be formed from similar or the same materials.

At least two benefits may be realized by dissociating the dielectric member from the coupling member as described herein. First, by providing a coupling member that is discrete from the dielectric member, the coupling member may be able to absorb stresses imposed thereupon, rather than transmit such stress into the dialectic member. Second, the disclosed arrangement permits the use of materials that are better-suited to their function, for example, the dielectric member may be formed of porcelain while the coupling member may be formed of stainless steel. Continuing with the present example, porcelain may be well suited as a dielectric member because of its excellent insulative properties, yet may be poorly suited as a coupling member due to its brittleness. Conversely, stainless steel may be well-suited as a coupling member because of its toughness and strength, yet electrically conductive therefore unsuitable as a dielectric. The present disclosure provides a coupler that advantageously combines the benefits of these materials without the drawbacks of either material.

The dielectric member may be formed from any suitable non-conductive material, such as glass, porcelain, ceramic, or polymer material. The coupling member may be formed from any suitable material, such as stainless steel, that is configured to operably engage the proximal and distal radiating portion of the antenna assembly to the coupler. The coupling portion may be configured as a threaded sleeve for screw mounting of the radiating portions to the coupler. The coupling member may be rigidly joined to the dielectric member, or it may be loosely joined in a "floating" configuration.

In embodiments, the insulating member may have longitudinal symmetry, having a radial thickness that is non-uniform about the longitudinal axis. The insulating member may include a central portion radius similar to the radius of the outer conductor, a sleeve portion having a radius configured to engage the inner diameter of the coupling member, and an end portion having a radius configured to retain the coupling member. The transitions between differing radii may be stepped (discontinuous), or may be tapered (continuous). The end portion may include a bevel to facilitate placement of the coupling member onto the insulating member during manufacturing.

The sleeve portion may include at least one longitudinal rib that is configured to engage a corresponding slot in the threaded coupling member. In this arrangement, the rib may serve to limit or prevent movement of the coupling member with respect to the insulating member arising from, for example, torque applied to the coupling member during antenna assembly.

Alternatively, the coupling portion may be configured for frictionally mounting the radiating portions to the coupler. For instance, the coupling portion may include ribs, projections, depressions, and/or textures configured to facilitate the frictional or interference coupling of the radiating portion(s) of the antenna assembly to the coupler.

In embodiments, the coupling portion may include a generally cylindrical reinforcing collar which extends into a corresponding cylindrical recess provided by the insulating member. The reinforcing collar may add strength to thinner regions of the insulating member, and may additionally distribute stresses to thicker regions of the insulating member.

BRIEF DESCRIPTION OF THE DRAWINGS

The above and other aspects, features, and advantages of the present disclosure will become more apparent in light of the following detailed description when taken in conjunction with the accompanying drawings in which:

FIG. 2A shows an exploded, cross-sectional view of a representative variation of a microwave antenna assembly;

FIG. 2B shows a cross-sectional view of a representative variation of a microwave antenna assembly;

DETAILED DESCRIPTION

Figure 1:
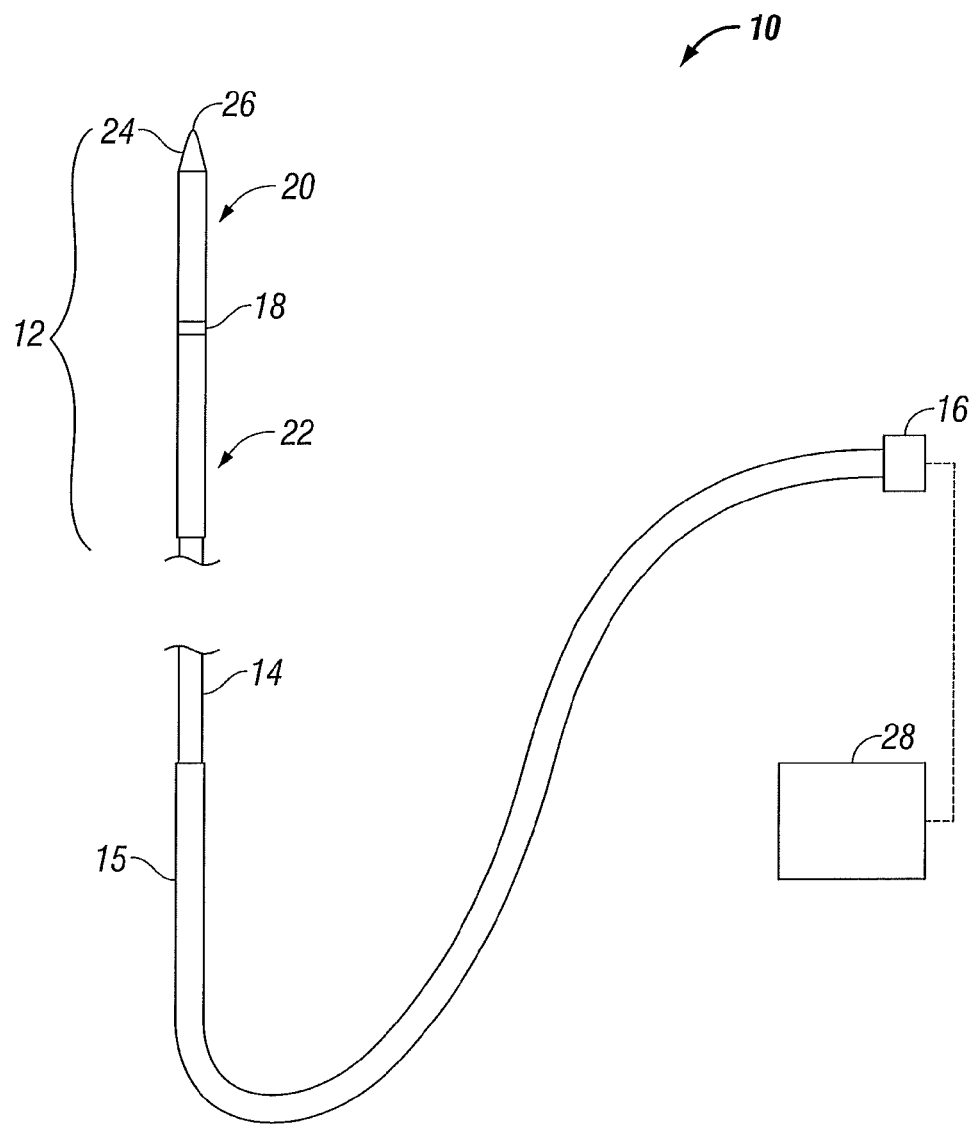
FIG. 1 shows a representative diagram of a variation of a microwave antenna assembly.

Particular embodiments of the present disclosure will be described herein with reference to the accompanying drawings. As shown in the drawings and as described throughout the following description, and as is traditional when referring to relative positioning on an object, the term "proximal" refers to the end of the apparatus that is closer to the user and the term "distal" refers to the end of the apparatus that is further from the user. In the following description, well-known functions or constructions are not described in detail to avoid obscuring the present disclosure in unnecessary detail.

FIG. 1 shows an exemplary embodiment of a microwave antenna assembly 10 in accordance with the present disclosure. The antenna assembly 10 includes a radiating portion 12 that is connected by feedline 14 (or shaft) via cable 15 to connector 16, which may further connect the assembly 10 to a power generating source 28, e.g., a generator. Assembly 10, as shown, is a dipole microwave antenna assembly, but other antenna assemblies, e.g., monopole or leaky wave antenna assemblies, may also utilize the principles set forth herein. Distal radiating portion 20 of radiating portion 12 may have a tapered end 24 which terminates at a tip 26 to allow for insertion into tissue with minimal resistance. Alternatively, tip 26 may be rounded or flat. Proximal radiating portion 22 is joined to distal radiating portion 20 by insulating coupler 18.

Figure 3:
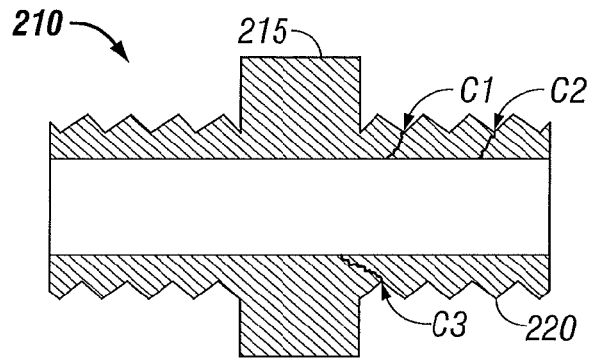
FIG. 3 shows a prior-art antenna coupler.

FIGS. 2A and 2B illustrate generally aspects of a prior art insulating coupler 210 configured to couple a proximal radiating portion 260 and a distal radiating portion 250 of a microwave antenna assembly 200. As seen in the exploded view of FIG. 2A and the assembled view of FIG. 2B, insulating coupler 210 includes a central portion 215 having an outer diameter similar to that of proximal radiating portion 260 and distal radiating portion 250. Prior art insulating coupler 210 further includes threaded coupling sections 220 and 225 that are configured to mate with corresponding internal threads 230 and 235 provided by the distal and proximal radiating portions, respectively. Prior art insulating coupler 210 may also include a channel 240 defined therein through which inner conductor 265 may pass from the proximal portion 260 to the distal portion 250 of antenna assembly 200. As can be seen in FIG. 3, prior art insulating coupler 210 may have drawbacks in that mechanical forces bearing upon threaded section 220 and/or threaded section 230 may cause mechanical failure of the coupler. For instance, cracks may form in prior art insulating coupler 210 as shown, by example only, at C1, C2 and C3. The cracks are particularly troublesome when the prior art coupler is formed from brittle material, where cracks may lead to fragmentation of the coupler, and/or sudden catastrophic failure of the antenna assembly.

Turning now to FIGS. 4-8, there is presented an improved high-strength microwave antenna coupler 400 in accordance with the present disclosure. Coupler 400 includes an insulating member 405 and at least one coupling member 460, 460'. Insulating member 405 may be formed from any suitable dielectric material, such as glass, porcelain, ceramic, or polymeric material. Insulating member 405 may include a central portion 410 having a radius similar to the radius of an outer conductor. Coupler 400 may further include at least one sleeve portion 420, 420' having a radius configured to engage the inner diameter 485 of coupling member 460, and, an end portion 425, 425' having a radius configured to retain the coupling member 460 to insulating member 405. A channel 430 may be disposed axially in the insulating member 405 for permitting the passage therethough of, for example without limitation, conductors, tubes, actuators, and the like.

Sleeve portion 420 may additionally include at least one longitudinal rib 450, 450' that is configured to engage with a corresponding longitudinal slot 470 defined in coupling member 460. Additionally or alternatively, coupling member 460 has defined upon the inner surface 485 thereof a longitudinal channel (not shown) configured to engage rib 450, 450'. Rib 450, 450' may extend from end face 426, 426' of end portion 425, 425' to central face 427, 427' of central portion 410. In embodiments, rib 450, 450' may extend from end face 426, 426' to an intermediate point between end face 426, 426' and central face 427, 427' (not shown). Additionally or alternatively, rib 450, 450' may extend from central face 427, 427' to an intermediate point between end face 426, 426' and central face 427, 427' (not shown). In embodiments, coupling member 460 may include exterior threads 462 for engaging coupler 400 to corresponding interior threads 481, 491 provided by radiating portion 480, 490.

The end portion may further include a bevel 440, 440' to facilitate joining of coupling member 460 to insulating member 405 during manufacture. For example, a method of manufacture is envisioned wherein a coupling member 460 to be joined with an insulating member 405 is axially aligned with insulating member 405 in a first step, and in a second step, slot 470 is indexed (i.e., rotationally aligned) with rib 450. In a third step, coupling member 460 is pressed onto insulating member 405. In greater detail, as coupling member 460 makes contact with end portion 425, the inner diameter 485 of coupling member 460 rides over bevel 440, thus widening slot 470 causing coupling member 460 to radially expand in a c-clamp like fashion, which permits coupling member 460 to ride over end portion 425. Additionally or alternatively, slot 470 may be temporarily widened by, for example, a tool, prior to being pressed onto sleeve 420, in order to ease the placement of coupling member 460 onto sleeve 420. Once coupling member 460 is fully pressed onto sleeve 420, i.e., positioned between end face 426 and central face 427, coupling member 460 clears end portion 425 whereupon the resiliency of coupling member 460 causes coupling member 460 to assume its original, unexpanded shape, thereby "locking" coupling member 460 into place on sleeve 420 between end face 426 and central face 427 and by the engagement of slot 470 with rib 450. It is contemplated that the steps of the method in accordance with the present disclosure can be performed in a different ordering than the ordering provided herein.

Figure 10:
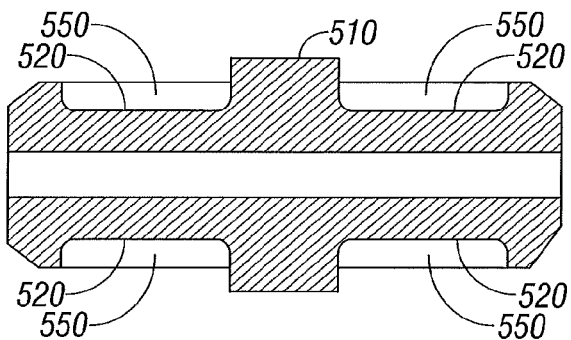
FIG. 10 shows a cross-sectional view of another embodiment of an antenna coupler insulating member in accordance with the present disclosure.
Figure 11A:
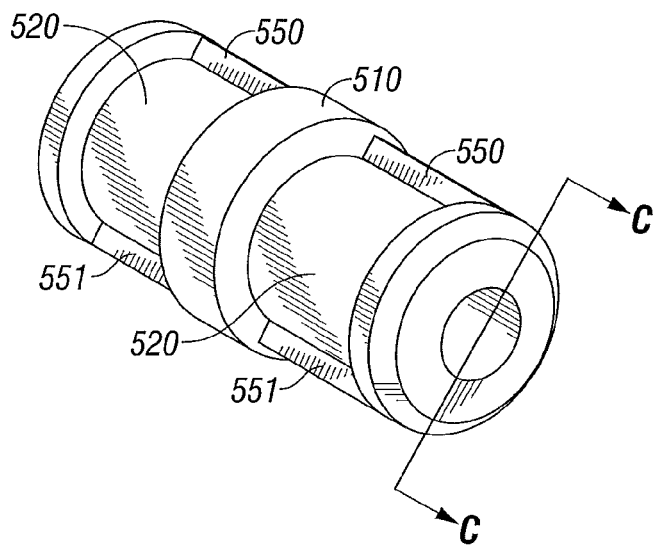
FIG. 11A shows an oblique view of an embodiment of the antenna coupler insulating member of FIG. 10 in accordance with the present disclosure.
Figure 11B:
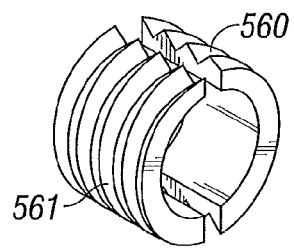
FIG. 11B shows an oblique view of a split coupling member in accordance with the present disclosure.

Turning now to FIGS. 10-11, embodiments according to the present disclosure are envisioned wherein opposing ribs 550 and 551 are provided by sleeve 520. In these embodiments, a split coupling member is provided wherein opposing semi-circular coupling members 560 and 561 are positioned on corresponding halves of sleeve 520. Semi-circular coupling members 560 and 561 may be retained on sleeve 520 by any suitable method, such as adhesive bonding, or additionally or alternatively, held in place by a fixture during manufacturing and held in place by the compressive force between coupling members 560, 561 and an outer conductor, i.e., a radiating portion of a microwave antenna assembly.

Figure 4:
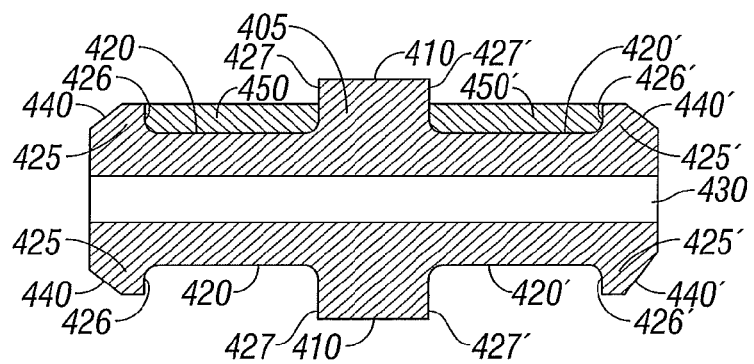
FIG. 4 shows a cross-sectional view of an embodiment of an antenna coupler insulating member in accordance with the present disclosure.
Figure 5:
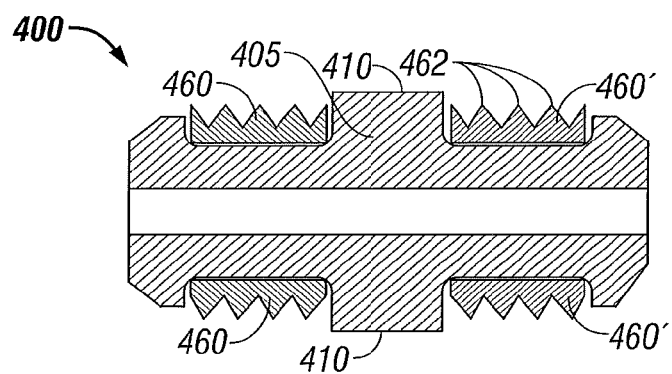
FIG. 5 shows a cross-sectional view of an embodiment of an antenna coupler in accordance with the present disclosure incorporating the insulating member of FIG. 4.
Figure 6:
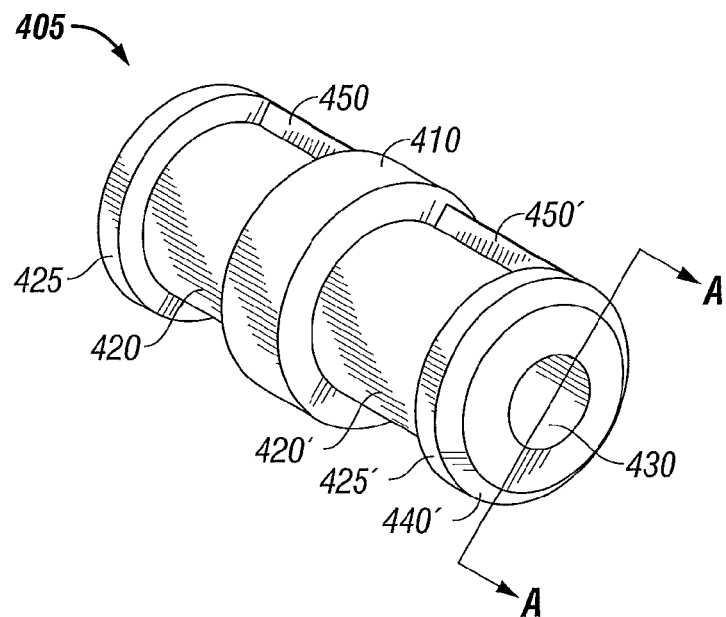
FIG. 6 shows an oblique view of the antenna coupler insulating member of FIG. 4 in accordance with the present disclosure.
Figure 7:
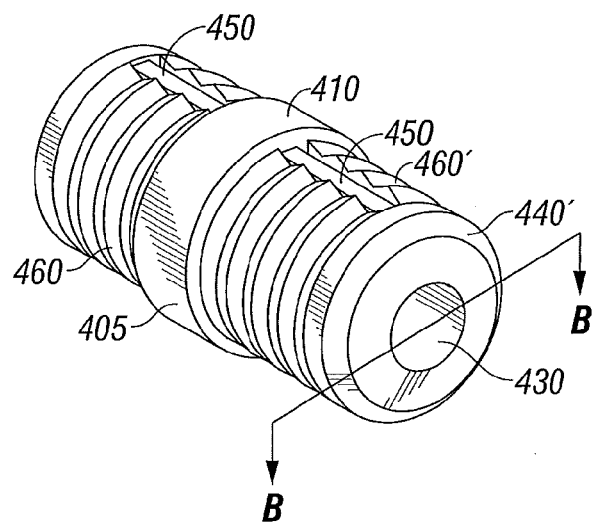
FIG. 7 shows an oblique view of the an antenna coupler of FIG. 5 in accordance with the present disclosure.
Figure 8A:
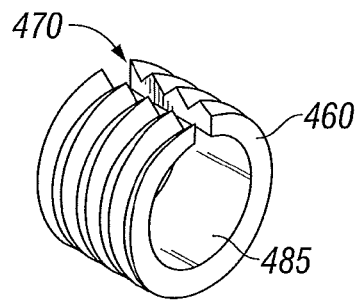
FIG. 8A shows an oblique view of a threaded coupling member in accordance with the present disclosure.
Figure 8B:
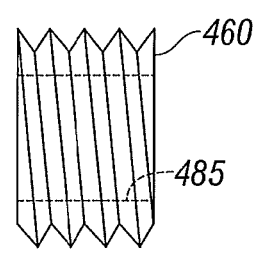
FIG. 8B shows a side view of the threaded coupling member of FIG. 8A in accordance with the present disclosure.
Figure 9:
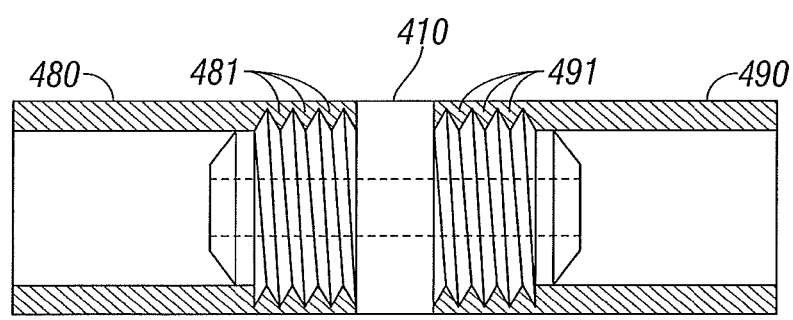
FIG. 9 shows a cross-sectional view of an embodiment of an antenna coupler in accordance with the present disclosure mated to distal and proximal radiating portions of a microwave antenna assembly.
Figure 12A:
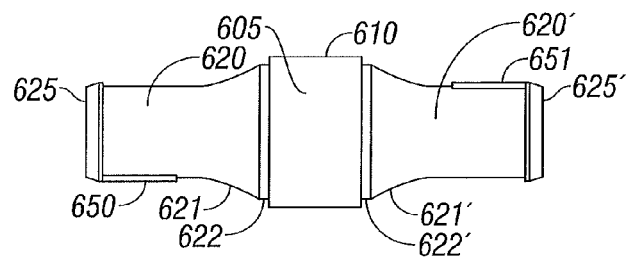
FIG. 12A shows a side view of yet another embodiment of an antenna coupler insulating member in accordance with the present disclosure.
Figure 12B:
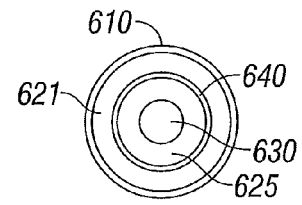
FIG. 12B shows an end view of the antenna coupler insulating member of FIG. 12A in accordance with the present disclosure.
Figure 13:
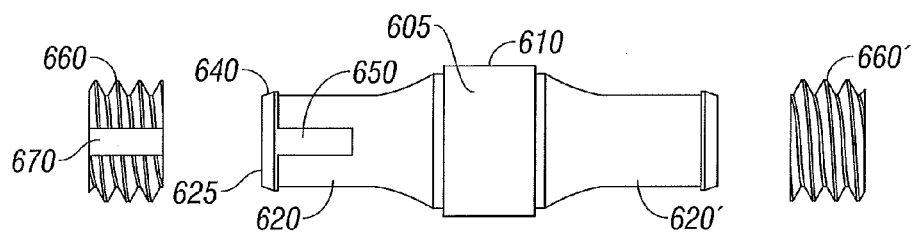
FIG. 13 is an exploded, top view of yet another embodiment of an antenna coupler in accordance with the present disclosure incorporating the antenna coupler insulating member of FIG. 12A.
Figure 14:
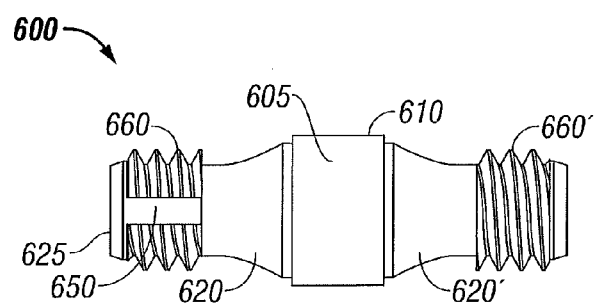
FIG. 14 is a top view of the antenna coupler of FIG. 13 in accordance with the present disclosure.

The transitions between differing radii may be stepped (discontinuous), as illustrated in FIGS. 4-5, or, may be tapered (continuous) as can be seen in the embodiments illustrated by FIG. 12 et seq. As best illustrated in FIGS. 12A and 12B, certain embodiments of a high-strength microwave antenna coupler 600 include an insulating member 605, which may include a tapered section 621, 621' between sleeve 620, 620' and a shoulder 622, 622'. A tapered section as described herein may strengthen insulating member 605 by, for example, dissipating stress concentrations which may otherwise be formed within insulating member 605, and/or reinforcing insulating member 605 with the additional material contained within tapered region 621, 621'. In embodiments, the transition between differing radii may be effectuated by a fillet.

Figure 17:
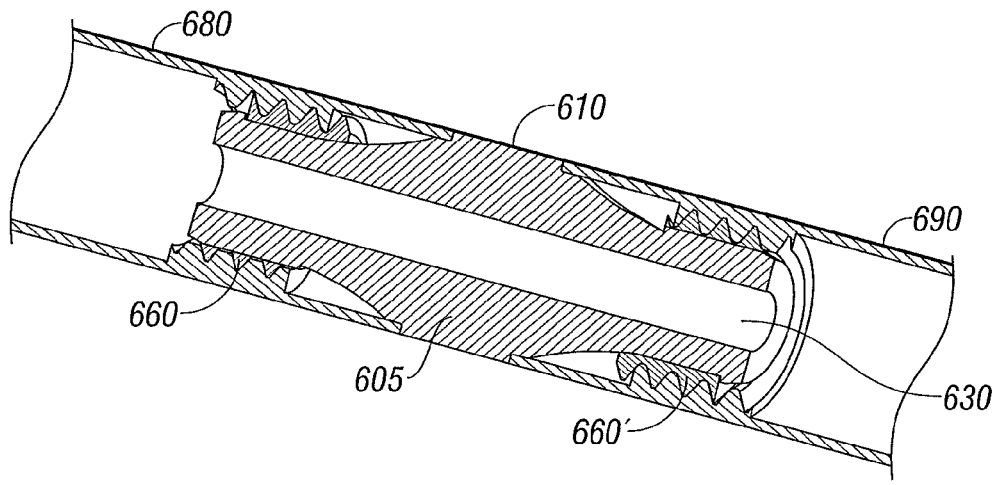
FIG. 17 is an oblique, cutaway view of the antenna coupler of FIG. 13 mated to distal and proximal radiating portions of a microwave antenna assembly in accordance with the present disclosure.
Figure 18:
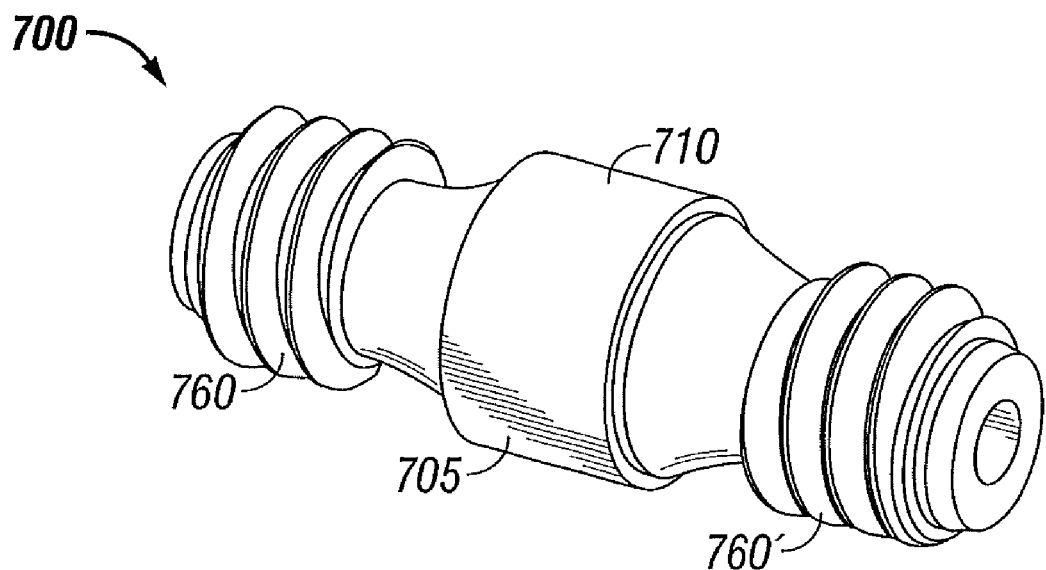
FIG. 18 is an oblique view of yet another antenna coupler in accordance with the present disclosure.
Figure 19:
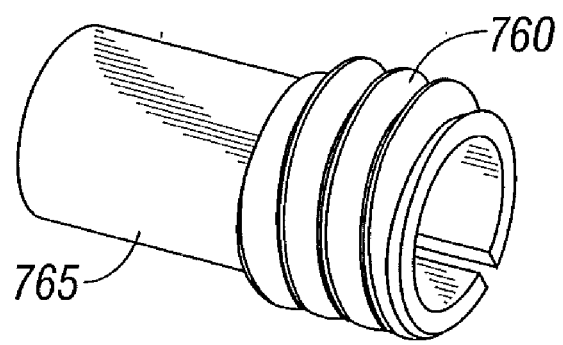
FIG. 19 shows an oblique view of a threaded coupling member having a reinforcing collar in accordance with the present disclosure.
Figure 20:
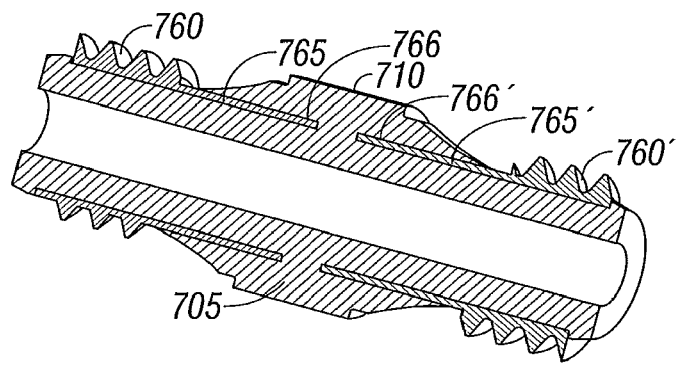
FIG. 20 is an oblique, cutaway view of the antenna coupler of FIG. 18 incorporating the threaded coupling member of FIG. 19 in accordance with the present disclosure.
Figure 21:
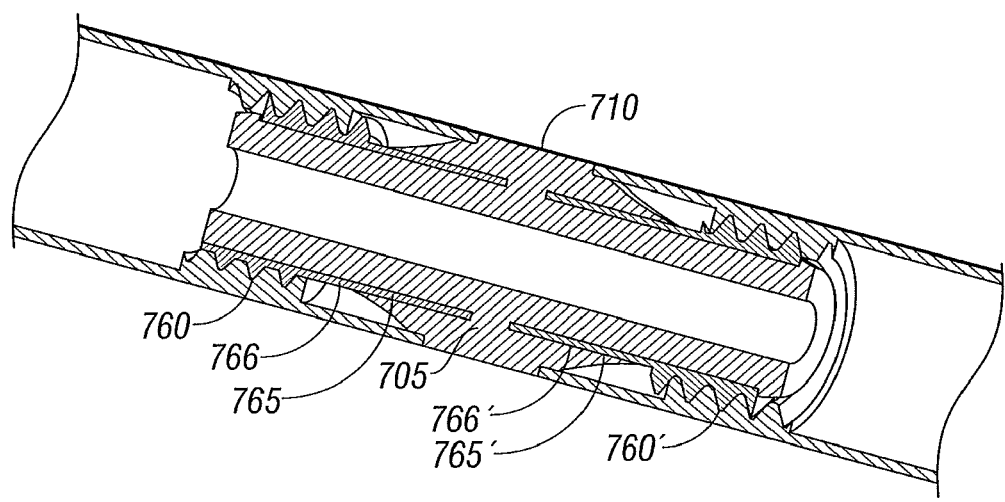
FIG. 21 is an oblique, cutaway view of the antenna coupler of FIG. 18 mated to distal and proximal radiating portions of a microwave antenna assembly in accordance with the present disclosure.

Insulating member 605 may include a central portion 610 having a diameter similar to the outside diameter of an outer conductor, e.g., the outside diameter of radiating portion 680, 690. Insulating member 605 may include a shoulder 622, 622'. In embodiments, shoulder 622, 622' may have a diameter dimensioned to provide a suitable fit, such as a interference fit, between shoulder 622, 622' and with the inside diameter of an outer conductor, as shown in FIG. 17.

Figure 15:
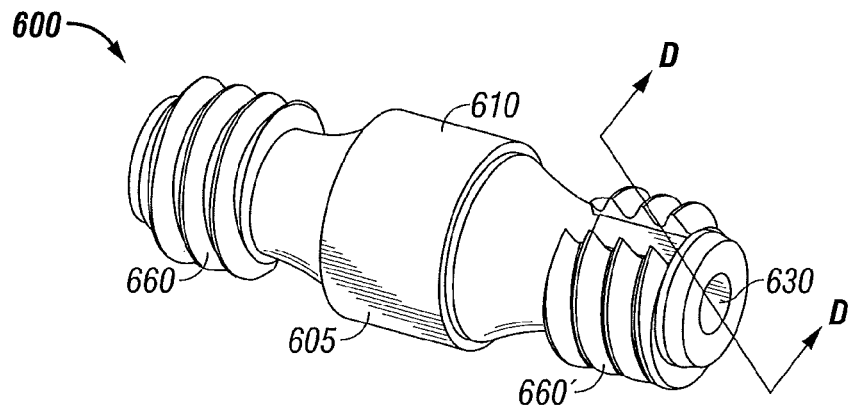
FIG. 15 is an oblique view of the antenna coupler of FIG. 13 in accordance with the present disclosure.
Figure 16:
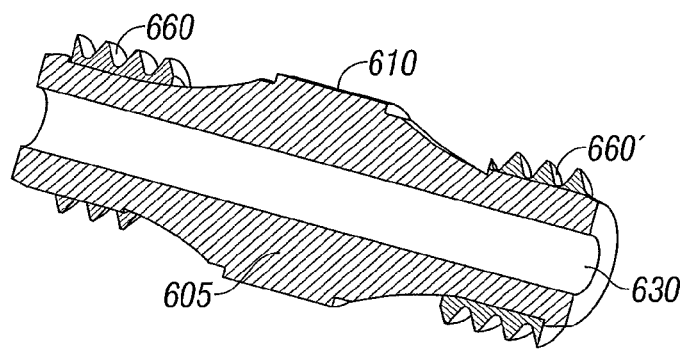
FIG. 16 is an oblique, cutaway view of the antenna coupler of FIG. 13 in accordance with the present disclosure.

High-strength microwave antenna coupler 600 may additionally include at least one coupling member 660, 660'. Sleeve portion 420, 420' may have a radius configured to engage the inner diameter (not explicitly shown) of coupling member 660, and, an end portion 625, 625' having a radius configured to retain the coupling member 660 to insulating member 605. As shown in FIGS. 15 and 16, a channel 630 may be disposed axially in the insulating member 605 for permitting the passage therethough of, for example without limitation, conductors, tubes, actuators, and the like. Coupling member 660 may be joined with an insulating member 605 in the manner previously described herein.

In another aspect best illustrated in FIG. 12A, a rib 650 is provided on one sleeve of the insulating member 605, for example, the distal sleeve, that is positioned 180° (measured as an angle around the longitudinal axis of insulating member 605) from a corresponding rib 651 provided on the opposite sleeve of insulating member 605. In these embodiments, coupling member 660 is rotationally oriented such that slot 670 is aligned with the corresponding rib 650.

With reference now to FIGS. 18-21, a microwave antenna coupler 700 in accordance with the present disclosure includes a coupling member 760 having a substantially cylindrical reinforcing collar 765, and an insulating member 705 having a generally cylindrical slot 766 disposed therein dimensioned to operably engage collar 765. The extension of collar 765 into insulating member 705 may increase the strength of thinner regions of insulating member 705, and additionally or alternatively, may transfer stresses to thicker regions of insulating member 705, i.e., central region 710.

In embodiments, collar 765 may be formed integrally with coupling member 760 from any suitable material, such as stainless steel. Microwave antenna coupler 700 may be manufactured by any suitable process, for example without limitation, by an insert molding process or by a two-shot molding process. In an insert molding process, at least one coupling member 760 is introduced as an insert into a mold dimensioned to form insulating member 710. Coupling member 760 may be placed manually, or by automated means such as a robotic placing device. Thereafter, insulating material is injected or otherwise introduced into the mold to form insulating member 710 in situ with coupling member 760. Insulating member 705 may be formed from polymeric materials using injection molding. Alternatively, insulating member 710 may be formed from ceramic materials, such as aluminum oxide ceramics.

For example, dry powder insert molding technique may be used to form insulating member 710 wherein a mechanical or hydraulic press compacts component ceramic powder. In other embodiments, insulating member 710 may be formed by an insert casting process wherein liquid ceramic material is injected into an elastomeric mold which may additionally retain and position coupling members 760, 760' for insert casting. Thereafter, insulating member 710 may optionally be fired to set or harden the ceramic material. Composite materials, which may include ceramic and polymeric components, may also be advantageously used to form insulating member 705.

The described embodiments of the present disclosure are intended to be illustrative rather than restrictive, and are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. A microwave antenna coupler, comprising:
   a cylindrical first member that includes:
   a central portion having a first diameter;
   at least one end portion having a second diameter that is less than the first diameter;
   at least one sleeve portion, disposed between the central portion and the at least one end portion, having a third diameter that is less than the second diameter, wherein the at least one sleeve portion includes at least one rib disposed longitudinally thereupon; and
   at least one second member disposed around the at least one sleeve portion, the at least one second member having a longitudinal slot defined therein dimensioned to operably engage the at least one rib;
   wherein the at least one second member includes a substantially cylindrical reinforcing collar;
   wherein the cylindrical first member has defined therein a substantially cylindrical slot adapted to operably engage the substantially cylindrical reinforcing collar.

2. The microwave antenna coupler according to claim 1, wherein an outer surface of the at least one second member is substantially threaded.

3. The microwave antenna coupler according to claim 1, wherein an outer diameter of the at least one end portion of the cylindrical first member includes a bevel.

4. The microwave antenna coupler according to claim 1, wherein a channel is defined axially through the cylindrical first member.

5. The microwave antenna coupler according to claim 1, wherein the cylindrical first member is formed from dielectric material.

6. The microwave antenna coupler according to claim 5, wherein the dielectric material is selected from the group consisting of glass, porcelain, ceramic, and polymeric material.

7. The microwave antenna coupler according to claim 1, wherein the at least one second member is formed from stainless steel.

8. The microwave antenna coupler according to claim 1, wherein a transition area is defined between said first and third diameters, or said second and third diameters, the transition area being at least one of stepped, filleted, and tapered.

9. The microwave antenna coupler according to claim 1, wherein the at least one end portion further comprises at least two end portions, and the at least one portion further comprises at least two sleeve portions including at least a first sleeve portion having at least a first rib and a second sleeve portion having at least a second rib.

10. The microwave antenna coupler according to claim 9, wherein the central portion is disposed between the at least a first sleeve portion and the at least a second sleeve portion, wherein a longitudinal axis is defined along the first member and wherein the first rib on the first sleeve portion is positioned along the longitudinal axis and wherein the second rib on the second sleeve portion is positioned 180° relative to the rib of the first sleeve portion along the longitudinal axis.

11. A microwave antenna coupler, comprising:
a cylindrical first member that includes:
a central portion having a first diameter;
at least one end portion having a second diameter that is less than the first diameter;
at least one sleeve portion, disposed between the central portion and the at least one end portion, having a third diameter that is less than the second diameter, wherein the at least one sleeve portion includes at least one rib disposed longitudinally thereupon; and
at least one second member disposed around the at least one sleeve portion, the at least one second member having a longitudinal slot defined therein dimensioned to operably engage the at least one rib;
wherein the at least one end portion further comprises at least two end portions, and the at least one sleeve portion further comprises at least two sleeve portions including at least a first sleeve portion having at least a first rib and a second sleeve portion having at least a second rib;
wherein, the central portion is disposed between the at least a first sleeve portion and the at least a second sleeve portion;
wherein a longitudinal axis is defined along the cylindrical first member and wherein the first rib on the first sleeve portion is positioned along the longitudinal axis and wherein the second rib on the second sleeve portion is positioned 180° relative to the rib of the first sleeve portion along the longitudinal axis.

12. The microwave antenna coupler according to claim 11, wherein an outer surface of the at least one second member is substantially threaded.

13. The microwave antenna coupler according to claim 11, wherein an outer diameter of the at least one end portion of the cylindrical first member includes a bevel.

14. The microwave antenna coupler according to claim 11, wherein a channel is defined axially through the cylindrical first member.

15. The microwave antenna coupler according to claim 11, wherein the cylindrical first member is formed from dielectric material.

16. The microwave antenna coupler according to claim 15, wherein the
dielectric material is selected from the group consisting of glass, porcelain, ceramic, and polymeric material.

17. The microwave antenna coupler according to claim 11, wherein the at least one second member is formed from stainless steel.

18. The microwave antenna coupler according to claim 11, wherein a transition area is defined between said first and third diameters, or said second and third diameters, the transition area being at least one of stepped, filleted, and tapered.

19. The microwave antenna coupler according to claim 11, wherein the at least one second member includes a substantially cylindrical reinforcing collar.

20. The microwave antenna coupler according to claim 19, wherein the cylindrical first member has defined therein a substantially cylindrical slot adapted to operably engage the substantially cylindrical reinforcing collar.

21. A method of manufacturing a microwave antenna coupler, comprising:
providing a cylindrical first member that includes:
a central portion having a first diameter;
at least one end portion having a second diameter that is less than the first diameter;
at least one sleeve portion, disposed between the central portion and the at least one end portion, having a third diameter that is less than the second diameter, wherein the at least one sleeve portion includes at least one rib disposed longitudinally thereupon;
providing at least one cylindrical second member configured to operably engage the at least one sleeve portion of the cylindrical first member, the at least one cylindrical second member having a longitudinal slot defined therein dimensioned to operably engage the at least one rib;
wherein the at least one second member includes a substantially cylindrical reinforcing collar;
wherein the cylindrical first member has defined therein a substantially cylindrical slot adapted to operably engage the substantially cylindrical reinforcing collar;
aligning axially the cylindrical first member with the at least one cylindrical second member;
indexing the longitudinal slot to the at least one rib;
pressing the at least one cylindrical second member onto the at least one sleeve portion of the cylindrical first member, such that the substantially cylindrical reinforcing collar is received in the substantially cylindrical slot of the cylindrical first member.

22. The method according to claim 21, further comprising:
increasing clearance between the at least one cylindrical second member and the cylindrical first member by causing the slot to be widened during the pressing step.

* * * * *